United States Patent [19]
Pai

[11] Patent Number: 5,727,273
[45] Date of Patent: Mar. 17, 1998

[54] ELECTRIC TOOTHBRUSH ASSEMBLY WITH STERILIZING AND CHARGING DEVICES

[76] Inventor: Chung-Jeng Pai, No. 10, Lane 423, Ching Shin Street, Chung Ho, Taipei Hsien, Taiwan

[21] Appl. No.: 787,940

[22] Filed: Jan. 23, 1997

[51] Int. Cl.⁶ ............................. A46B 13/02; A61L 2/16
[52] U.S. Cl. .................... 15/22.1; 15/28; 422/300
[58] Field of Search ....................... 422/300, 305; 15/257.01, 22.1

[56] References Cited

U.S. PATENT DOCUMENTS

| | | | |
|---|---|---|---|
| 1,283,403 | 10/1918 | Eustis | 422/300 |
| 2,038,941 | 4/1936 | Koch | 422/300 |
| 2,129,150 | 9/1938 | Pekrov | 422/300 |
| 3,478,758 | 11/1969 | Davies | 422/300 |
| 3,955,922 | 5/1976 | Moulthrop | 422/300 |
| 4,625,119 | 11/1986 | Murdoch, III | 422/300 |
| 5,487,877 | 1/1996 | Choi | 422/300 |

*Primary Examiner*—Randall Chin
*Attorney, Agent, or Firm*—Bacon & Thomas

[57] ABSTRACT

An electric toothbrush assembly with sterilizing and charging devices including a housing, a battery casing and an electric toothbrush. The housing is equipped with an ozone unit and a charging unit. The battery casing may be inserted into the electric toothbrush to provide a supply of power.

9 Claims, 10 Drawing Sheets

ELECTRIC TOOTHBRUSH ASSEMBLY WITH STERILIZING AND CHARGING DEVICES

BACKGROUND OF THE INVENTION (a) Field of the invention

The present invention relates generally to an electric toothbrush, and more particularly to an electric toothbrush assembly with sterilizing and charging devices.

(b) Description of the Prior Art

Like ordinary toothbrushes, electric toothbrushes may accumulate dirt and scum, which must be cleaned up to prevent germs. Electric toothbrushes generally used with dry battery cells, which must be replaced from time to time. Improper disposal of battery cells may pollute the environment. Although electric toothbrushes may be used with rechargeable batteries or connected to a charger, it is expensive to purchase all the related accessories, which are space-occupying as well.

SUMMARY OF THE INVENTION

A primary object of the present invention is to provide an electric toothbrush assembly which is equipped with a charging unit, and an ozone unit for sterilizing purposes.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

As shown in the drawings, the present invention essentially comprises an assembly body 1, a battery casing 2 (in FIG. 3), and an electric toothbrush 3.

Figure 1:
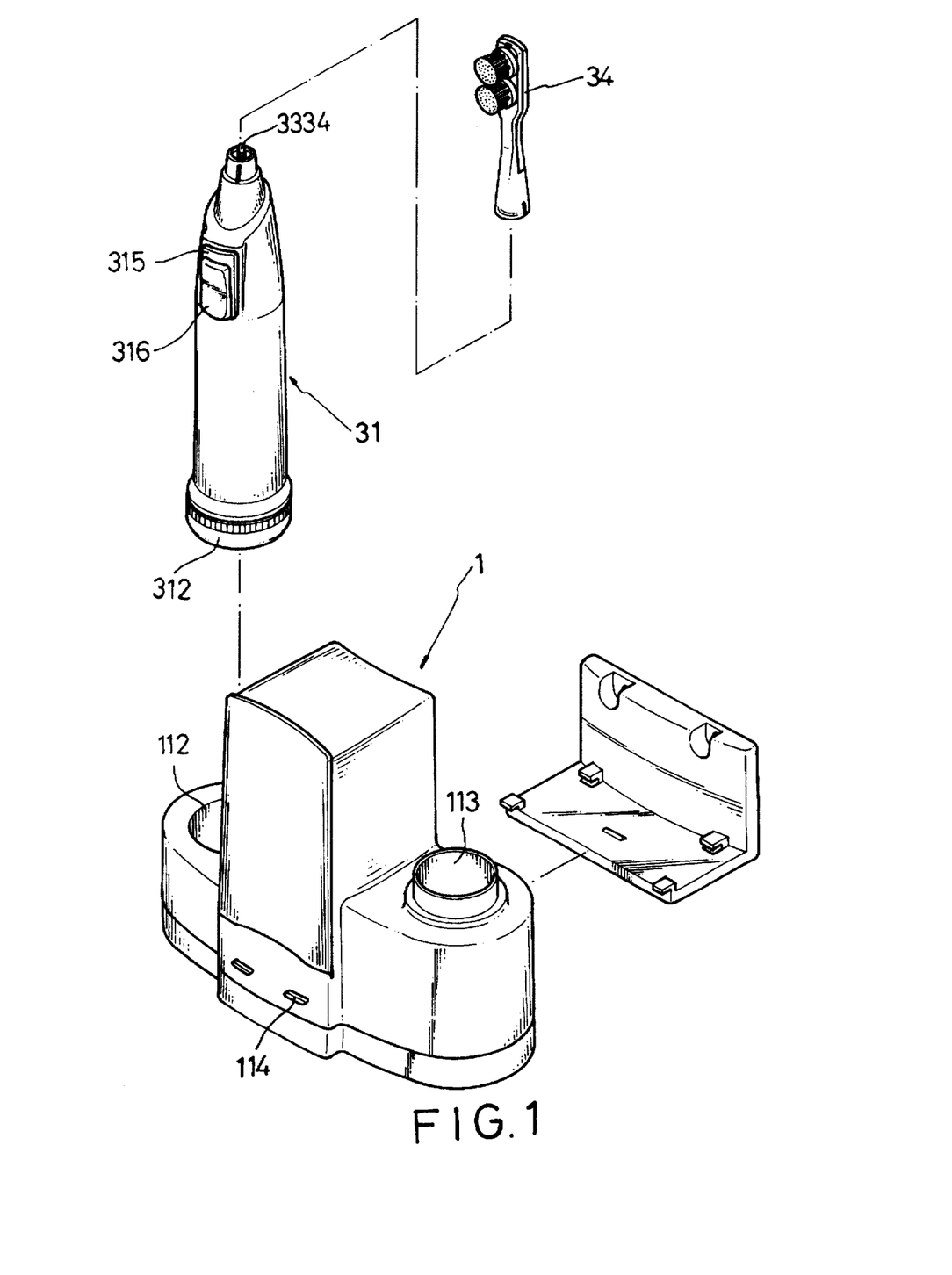
FIG. 1 is a schematic view of the present invention, with the battery casing concealed inside the shell of the electric toothbrush.
Figure 2:
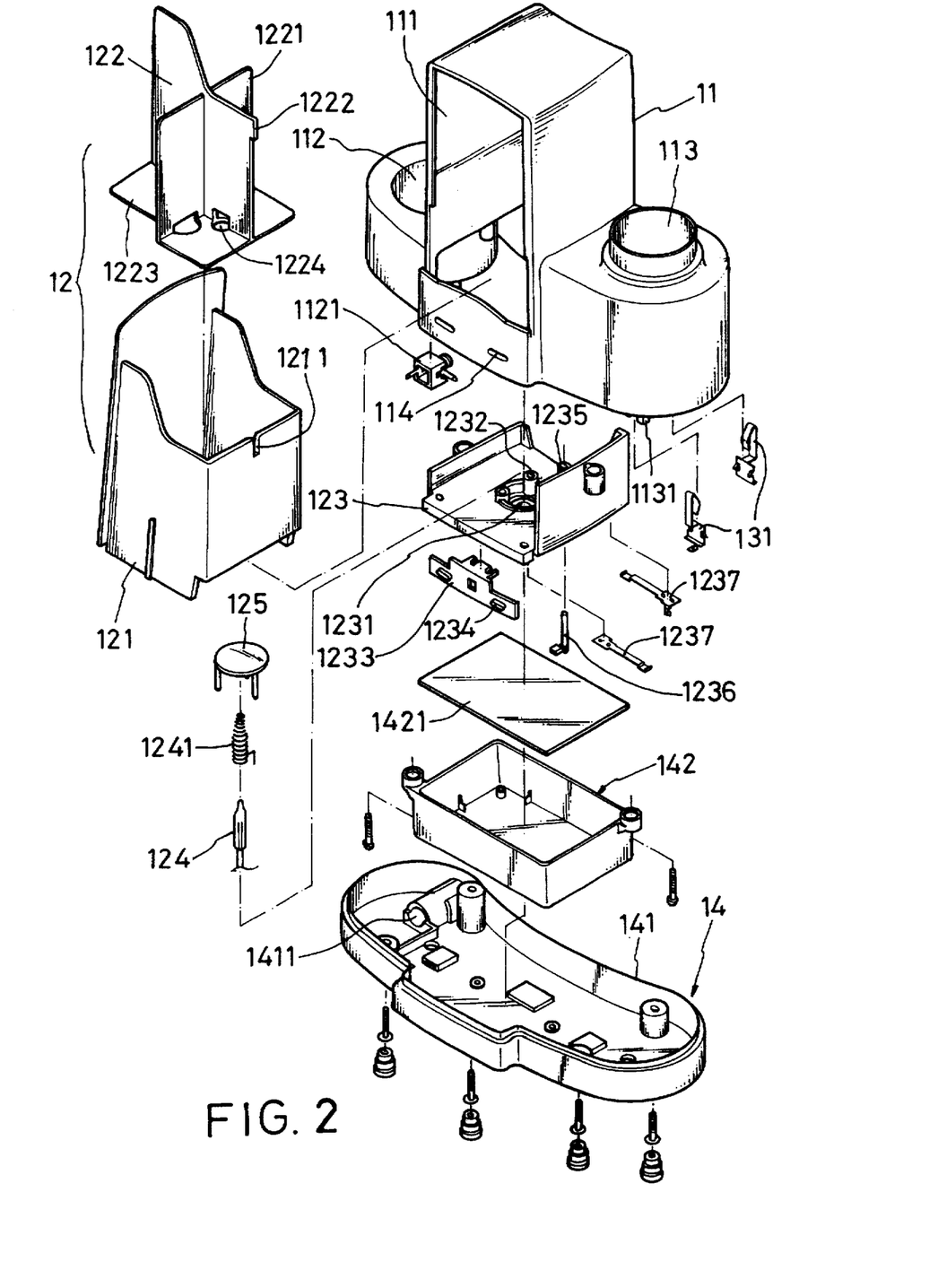
FIG. 2 is an elevational exploded view of the assembly body of the present invention.

The assembly body 1, as shown in FIG. 2, comprises a housing 11, an ozone unit 12, a charging unit 13, and a bottom casing 14.

The housing 11 has a hollow ozone chamber 111 in the middle. On the left thereof is a recess 112 for holding the electric toothbrush 3. On the right thereof is a charging chamber 113. In addition, at the housing wall below the ozone unit 111, there are two indication holes 114 for the light from indication lights to pass through. At the same time, the lower portion of the housing 11 is provided with pins and grooves or other means for securing with the bottom casing 14. As such belongs to the prior art, it will not be discussed herein. The bottom of the recess 112, on the other hand, extends downwardly to be connected to an electrical connector for connecting external power supply, which is connected by electric wires to the ozone unit 12 and the charging unit 13 to supply power thereto. Besides, two electrical connectors 1131 are provided at the bottom of the charging chamber 113, and the inner wall of the bottom of the charging chamber 113 are provided with two charging grooves 1132 in matching (see FIG. 4).

The ozone unit 12 comprises an ozone cylinder 121, an ozone partitioning element 122, a base plate 123, an ozone light 124, and an ozone lid 125. The ozone cylinder 121 is provided with a slit 1211 at the center of the upper portion of the inner wall thereof for engaging and thereby positioning a tab 1222 of one of a plurality of partition plates 1221 of the ozone partitioning element 122. The ozone partitioning element 122 is comprised of partition plates 1221 erected and connected at right angles to one another to divide into a plurality of compartments. A bottom plate 1223 of the ozone partitioning element 122 is provided with a bottom hole 1224 for passage of ozone thereinto. When the ozone partitioning element 122 is placed inside the ozone cylinder 121 with the tab 1222 abutting the lower end of the slit 1211 to stop further movement, the size of the ozone cylinder 121 matches that of the ozone chamber 111. Therefore, during insertion, the lower rim of the ozone cylinder 121 abuts the upper rim of the housing 11 at the indication holes 114 as support.

Figure 5:
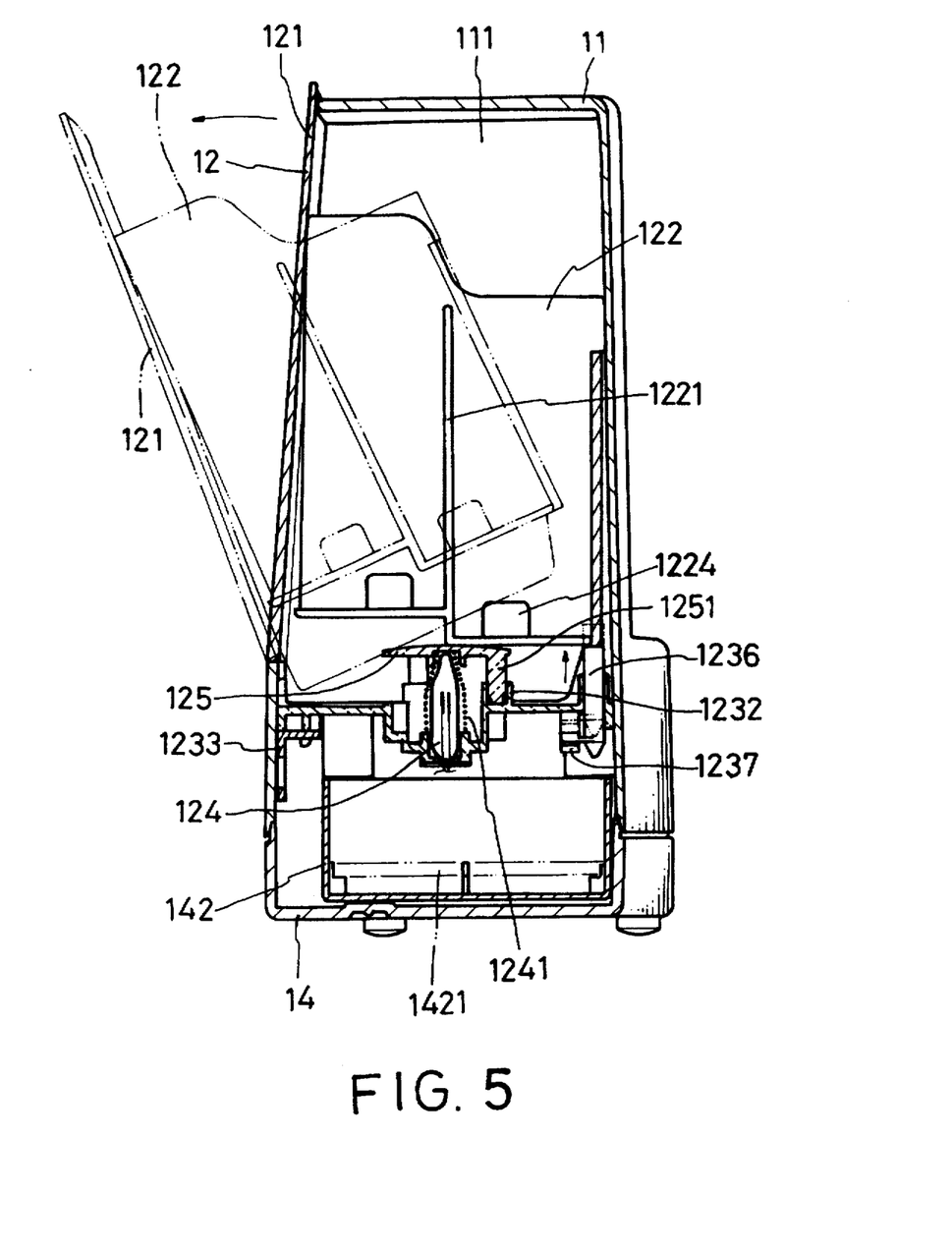
FIG. 5 is a schematic sectional view of the ozone unit of the present invention.

The base plate 123 is comprised of a plate having extended walls at opposite sides. Mounting holes are provided on the outer side of the extended walls for locking the base plate 123 to the bottom of the housing 1 below the ozone chamber 111. The base plate 123 has an ozone hole 1231 in the center with a plurality of hollow posts 1232 erected around it for coupling with the ozone lid 125. An indication light plate 1233 is locked to a front end of the base plate 123 and is provided with a plurality of indication lights 1234 and circuits connecting the power source. At the same time, a switch slot 1235 is provided at a rear end of the base plate 123 for passage of a switch lever 1236, as shown in FIG. 5. When the bottom of the rear rim of the ozone cylinder 121 touches and presses the switch lever 1236, two switch reeds 1237 will achieve contact and actuate the ozone light 124 so that the indication lights 1234 are on. The switch may also be provided with an automatic power interruption device or a timed starting device. All this belongs to the prior art and is not discussed herein.

The ozone light 124 is a neon light connected to the power source. It may be wrapped in a spring 1241 for protection purposes. In practice, it passes through the ozone hole 1231.

The ozone lid 125 has a plurality of mounting pins 1251 for insertion into the hollow posts 1232 around the ozone hole 1231 for positioning purposes.

Figure 4:
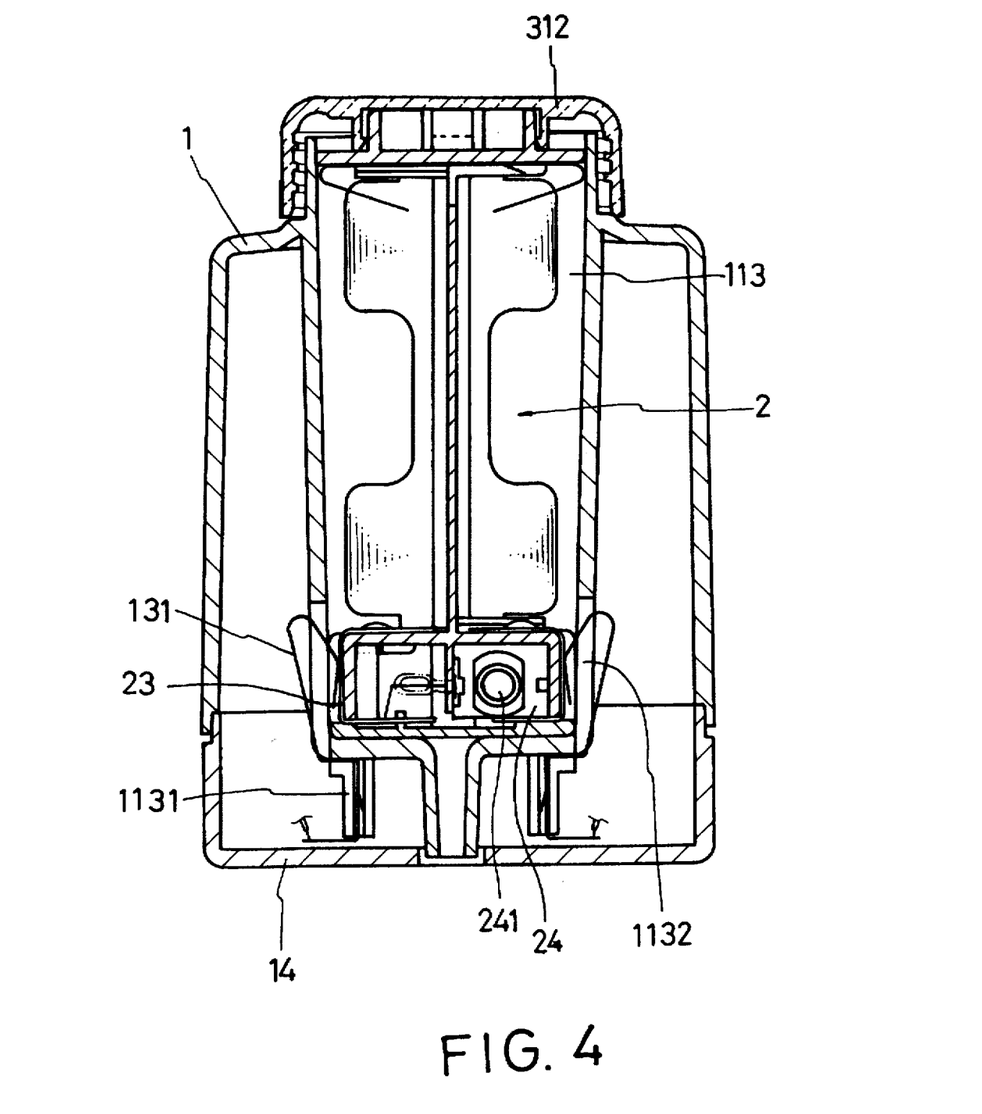
FIG. 4 is a schematic sectional view of the charging unit of the present invention.

The charging unit 13 essentially comprises two charging reeds 131 inserted and positioned at the electrical connectors 1131 at the bottom of the charging chamber 113 of the housing 11. They extend from the charging grooves 1132 into the charging chamber 113. Each charging reed 131 is connected to the power source by a conventional circuit.

The bottom casing 14 is comprised of a bottom 141 and a cover 142. The bottom 141 is an open-top casing having a size matching the bottom portion of the housing 11 so that it may be locked to the bottom portion of the housing 11 by conventional means such as posts and holes. The bottom 141 is provided with a power source hole 1411 at a position corresponding to that of the electrical connector 1121 of the housing 11 for passage of electrical wires or terminals.

The cover 142 is an open-top box-like structure with side mounting holes for locking with the housing 11. A circuit board 1421 is disposed on top of the cover 142 for supply of electric power and control of circuits.

After the assembly body 1 is assembled. The ozone chamber 111 may be filled with ozone by means of the ozone unit 12 so that the tooth brush placed in the ozone cylinder 121 may be cleaned and sterilized. The charging chamber 113 on the right side of the assembly body 1 may allow charging of the battery casing 2 of the electric toothbrush 3. In addition, the recess 112 may hold the handle portion of the electric toothbrush 3. Thus, the present invention achieves multiple purposes in a single assembly body.

Figure 3:
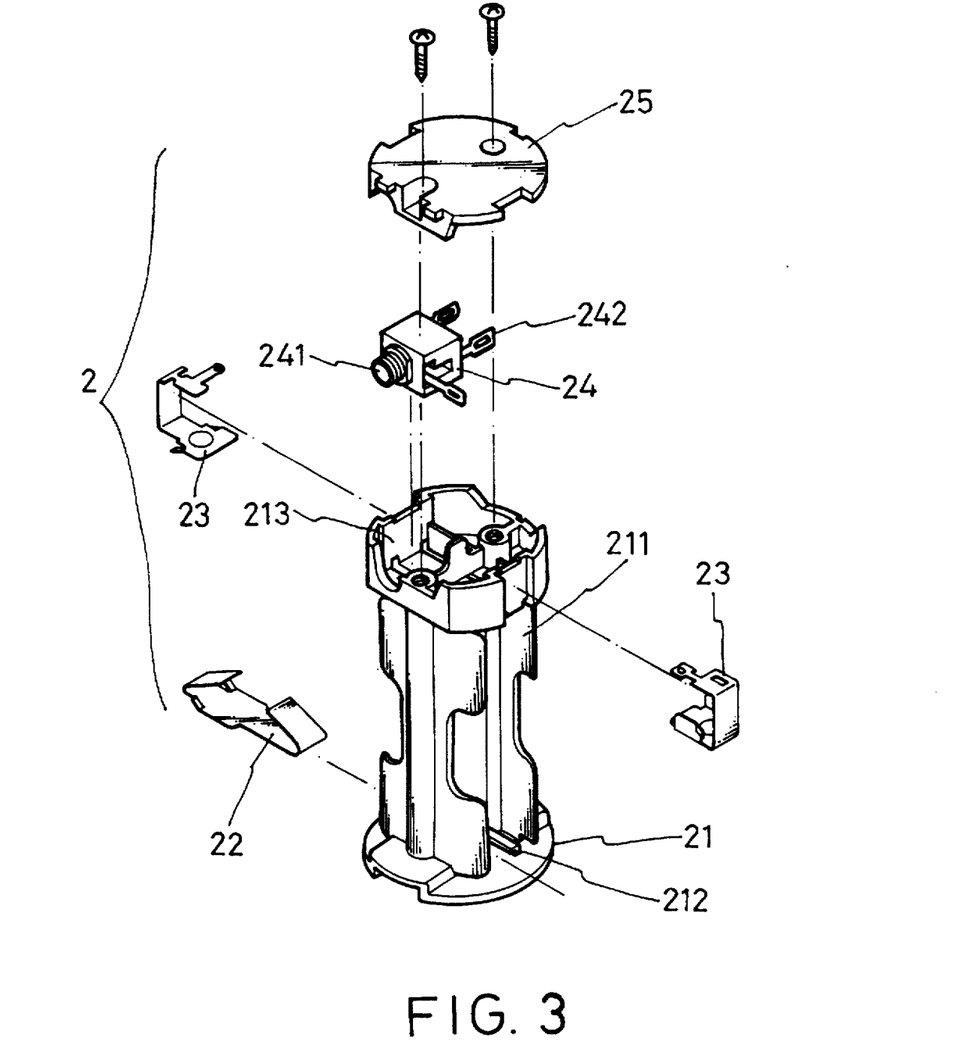
FIG. 3 is an elevational exploded view of the battery casing of the present invention.

The battery casing 2, referring to FIG. 3, essentially comprises a cylindrical body 21, a lower conductive plate 22, two upper conductive plates 23, a charging terminal 24, and a cover 25.

The cylindrical body 21 is provided with two pairs of oppositely oriented curved wings 211 mounted in a vertical manner for tightly holding the battery cells. Two parallel tracks 212 are provided on the upper side of the bottom for positioning the lower conductive plate 22. A terminal chamber 213 is formed at an upper portion of the cylindrical body 21 for accommodating the charging terminal 24. The cylindrical body 21 is also provided with conventional means for locking with the cover 25.

The lower conductive plate 22 is a metallic electrically conductive plate inserted into the tracks 212 with its ends bending upwardly to achieve resilient contact with the battery cells.

The upper conductive plates 23 are also metallic electrically conductive plates and are in contact with the charging terminal 24. The charging terminal 24 has an end hole 241 for insertion of an external terminal, and a couple of extended wings 242 for connecting the upper conductive plates 23 to achieve electrical connection.

The cover 25 is a plate structure having a size matching the upper side of the cylindrical body 21. It is locked to the cylindrical body 21 by screws. During charging, the battery casing 2 is inserted upside down into the charging chamber 113, as shown in FIG. 4, so that the upper conductive plates may contact the charging reed 131 to make the connection. When external power is used for charging, it is only necessary to insert the external terminal into the end hole 241 of the charging terminal 24. For charging, nickel-cadmium cells may be used. Ordinary dry cells may also do.

When the brush portion 34 of the electric toothbrush 3 is placed inside the ozone cylinder 121, the latter is tilted rearwardly to allow closing. When the switch lever 1236 is touched, the ozone light 124 is caused to be on to generate ozone for sterilizing the brush portion 34, as shown in FIG. 5. The battery casing 2 is inserted into the charging chamber 113 for recharging purposes, as shown in FIG. 4.

Figure 6:
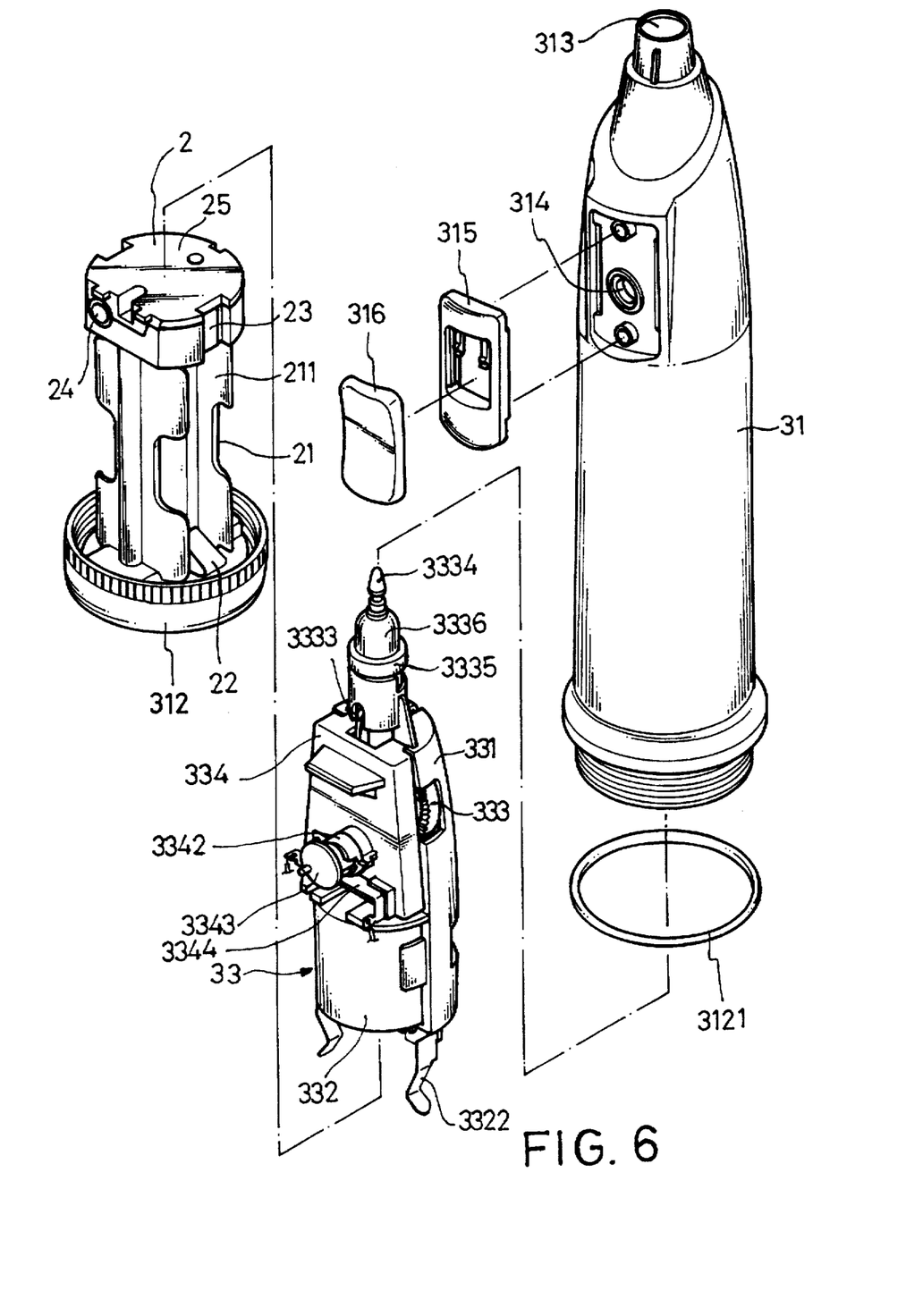
FIG. 6 is an elevational exploded view of the electric toothbrush of the present invention.
Figure 8:
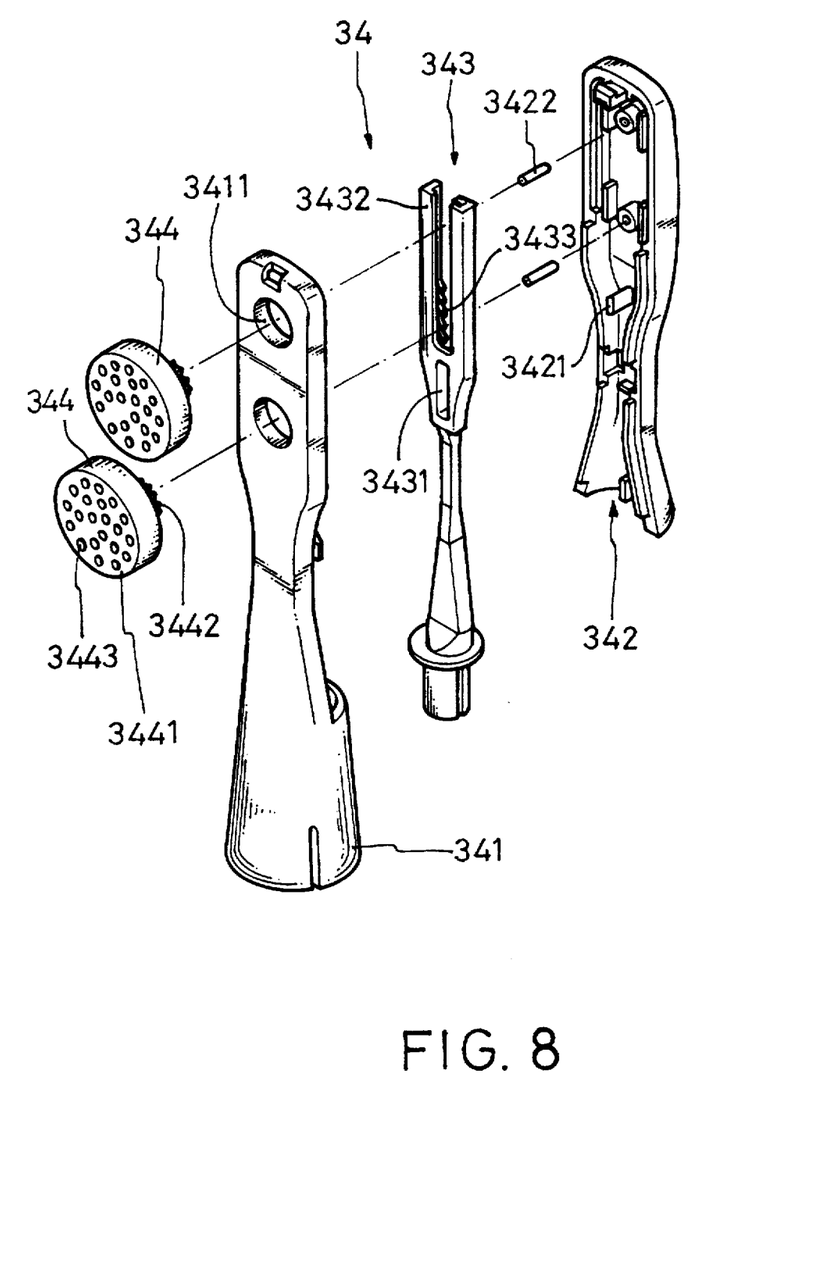
FIG. 8 is an elevational exploded view of the brush portion of the electric toothbrush of the present invention.
Figure 9:
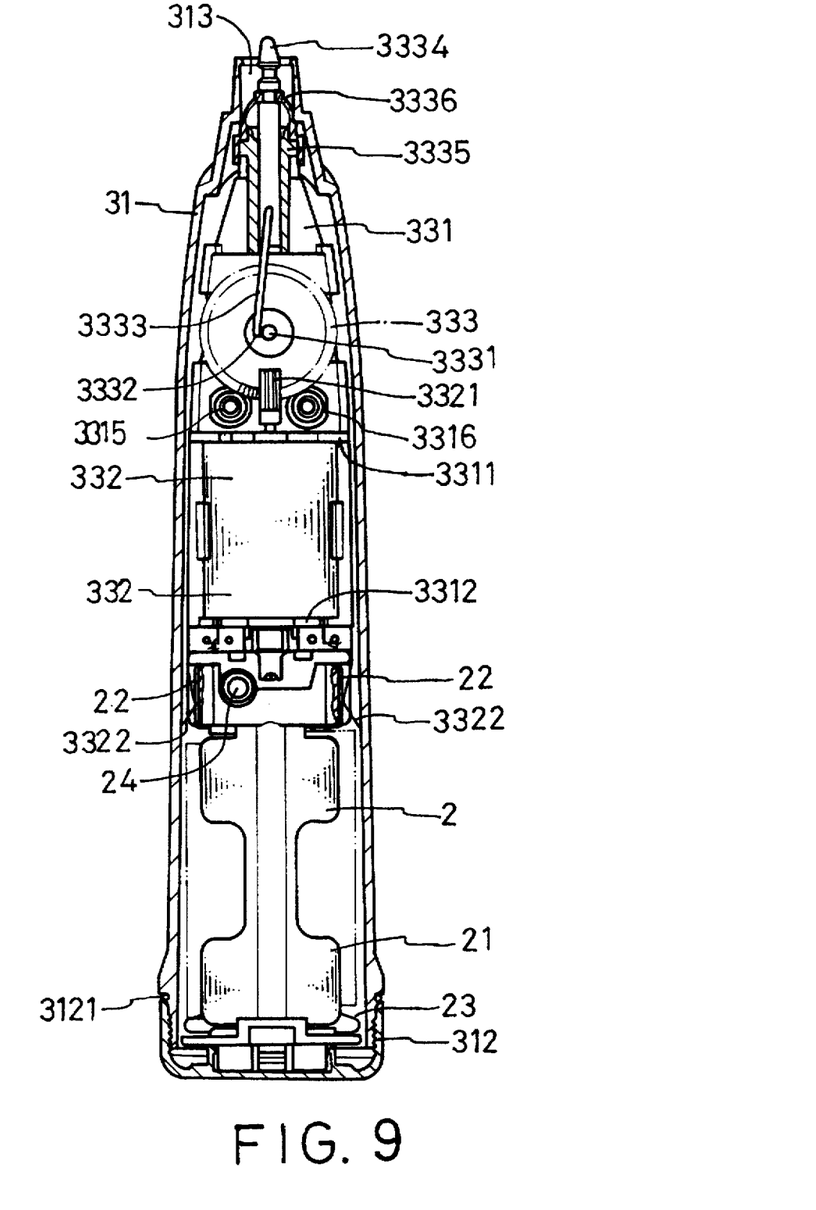
FIG. 9 is a schematic sectional view of the shell of the electric toothbrush of the present invention.
Figure 10:
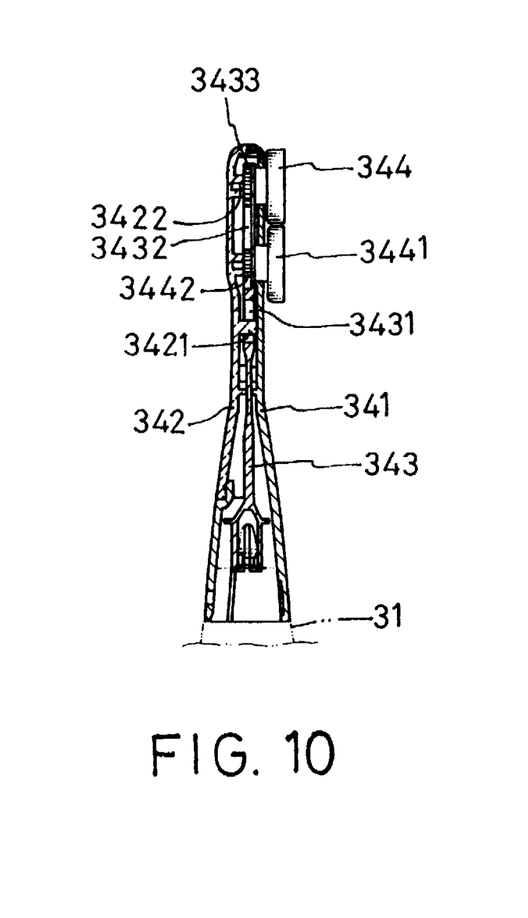
FIG. 10 is a schematic sectional view of the brush portion of the electric toothbrush of the present invention.

The electric toothbrush 3, as shown in FIG. 6, is comprised of a shell 31, the battery casing 2, a transmission portion 33, and the brush portion 34 (see FIG. 8).

Figure 7:
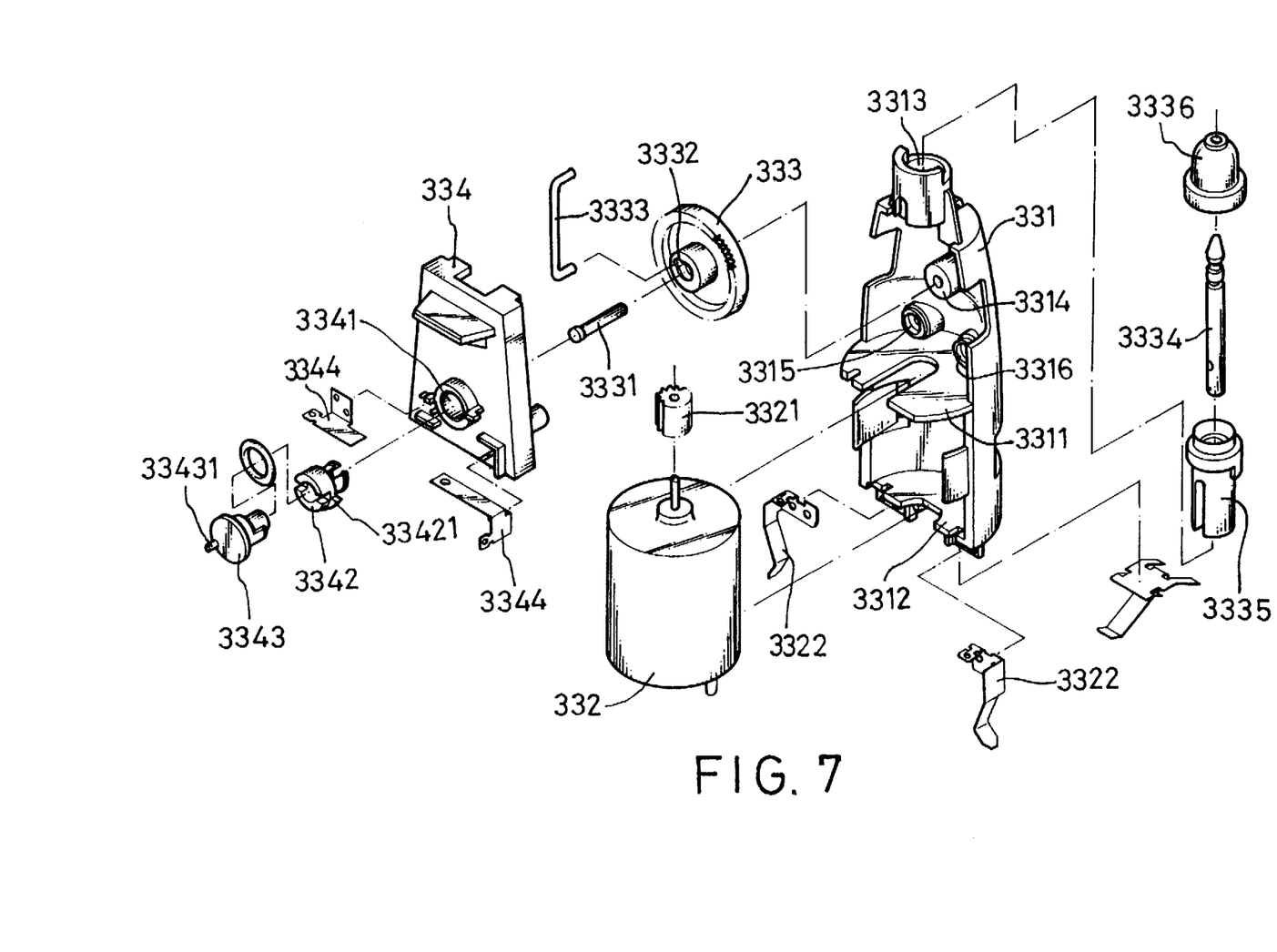
FIG. 7 is an elevational exploded view of the transmission portion of the electric toothbrush of the present invention.

With reference to FIG. 7, the shell 31 is an elongate hollow structure with an interior chamber 311 (not shown due to angle of projection) for accommodating the battery casing 2 and the transmission portion 33. The bottom portion is provided with a threaded section for screwable engagement with a shell bottom 312 for closing purposes. An elastic ring 3121 may further be provided for water-tightness. As such belongs to the prior art, it will not be discussed herein. The upper portion of the shell 31 tapers gradually upward to match the shape of the transmission portion 33, and has a hole 313 through which a transmission shaft 3334 may extend. In addition, a switch slot 314 is formed on the shell 31 and covered by a switch frame 315. A switch cover 316 is provided on the switch frame 315 for pressing purposes. In order that the battery casing 2 and the transmission 33 are positioned, the inner wall of the chamber 311 of the shell 31 is provided with ribs or grooves. As such also belongs to the prior art and is therefore not discussed herein.

The battery casing 2 is provided chiefly for supplying power to the transmission portion 33.

The transmission portion 33 is shaped like a shuttle and has an outer diameter matching the inner diameter of the shell 31 so that it may be accommodated therein. With reference to FIGS. 6 and 7, the transmission portion 33 is divided into an upper half and a lower half by a substantially hemispherical transmission shell 331 having a middle partition plate 3311 with a central slot. The bottom is provided with a bottom partition plate 3312 while a motor 332 is accommodated at the lower portion. The output axle of the motor is pivotally connected to an output gear 3321 and connected to the upper conductive plates 23 of the battery casing by means of two electrically conductive connecting plates 3322 of the transmission shell 331 for supply of electricity. Therefore, when the motor 332 is disposed between the middle partition plate 3311 and the bottom partition plate 3312, the output gear 3321 may extend through the slot of the middle partition plate 3311.

Additionally, the upper portion of the transmission shell 331 is provided with a hole 3313, and at one side therebelow are provided a mounting hole 3314, a locking hole 3315, and an insert hole 3316 for connection with relating components to be described hereinafter.

The output gear 3321 vertically engages a transmission gear 333 and is pivotally connected to the mounting hole 3314 by means of a spindle 3331. The axle of the transmission gear 333 is provided with an eccentric hole 3332 for insertion therein a substantially C-shaped pull arm 3333 having one end inserted into the hole of a transmission shaft 3334. The lower portion of the transmission shaft 3334 is fitted with a sleeve 3335 while the upper portion extends through a water-proof jacket 3336. The sleeve 3335 is inserted and fitted into the hole 3313 of the transmission shell 331.

Furthermore, a transmission cover 334 is disposed in the space above the middle partition plate 3311 and is secured by means of the locking hole 3315 and the insertion hole 3316. The transmission cover 334 is provided with a switch mounting hole 3341 at a suitable position. A switch cock 3342 is disposed in the switch mounting hole 3341. The periphery of the switch cock 3342 is provided with a curved projection 33421 of a larger diameter. A switch knob 3343 is inserted through the switch cock 3342 and the switch mounting hole 3341. A switch rod 33431 extends vertically from the switch knob 3343 into the insert hole of the switch cover 416 of the shell 31. At the same time, at both sides of the lower portion of the transmission cover 334, there are respectively provided an switch reed 3344 disposed in a horizontal fashion. The overlapping portion corresponds to the switch cock 3342. Therefore, when the curved projection 33421 presses the switch reed 3344 at the upper side, electrical connection is achieved. On the contrary, when the switch cock 3342 rotates and the curved projection 33421 is thus unable to press the switch reed 3344 at the upper side, the two switch reeds 3344 will become separated and cutting off the electrical connection.

Referring to FIG. 8, the brush portion 34 is comprised of a brush shell 341 and a brush cover 342 enveloping a brush stem 343, and two brush heads 344.

The brush shell 341 is cylindrical at the lower portion and is sized to match the upper end of the shell 31 so that they may be connected. It further has grooves or slots for matching the posts or other engaging means of the shell 31, which is well known in the art. Besides, in order that the brush cover 342 and the brush shell 341 may be engaged, ribs or mounting slots or the like may be provided. The brush shell 341 further has two openings 3411 in the upper portion for fitting the brush heads 344.

The brush cover 342 is sized to match the brush shell 341 so that they may be coupled. The middle of the brush cover 342 is provided with a pin 3421 for positioning the brush stem 343. Two posts 3422 are further provided at positions matching the openings 3411 of the brush shell 341 for securing the brush heads 344.

The brush stem 343 is an elongate rod with a hole in the center of its bottom side for receiving the transmission shaft 3334. The middle portion thereof is provided with an elongate slot 3431 for passage of the rod 3421 of the brush cover 342. The upper portion thereof is forked to form two parallel arms 3432 each of which has a toothed section at the upper or lower portion thereof. In other words, when one arm 3432 has the toothed section at the upper portion, the other arm 3432 will have the toothed section at the lower portion.

The brush heads 344 is comprised of a disk-shaped brush base 3441 having a brush wheel 3442 secured at the center of one side thereof. The pitch of the brush wheel 3342 correspond to that of the toothed section 3433 of the brush stem 343. In addition, the brush base 3441 has a plurality of holes 3443 for insertion of bristles or their equivalents (which are well known in the art).

In actual assembly, the brush shell 341 and the brush cover 342 enclose the brush stem 343 and the joint is sealed by ultrasonic waves.

Referring to FIGS. 6-8, in assembly, the transmission portion 33 is inserted into the shell 31 via the bottom side of the latter. The battery casing 2 is also inserted into the bottom of the shell 31 with the elastic ring 3121 and the bottom partition plate 3312 locked to the shell 31 and the switch cover 316 covering the switch frame 315. The brush portion 34 is fitted onto the upper end of the shell 31 by means of the brush shell 341, with the bottom side of the brush stem 343 fitted onto the transmission shaft 3334. The present invention is thus assembled.

Figure 11:
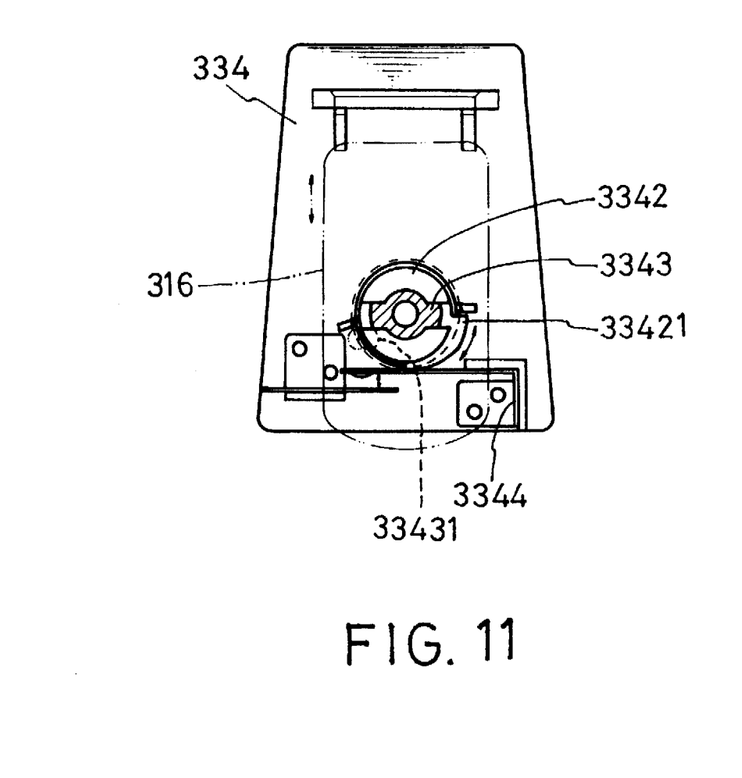
FIG. 11 is a sectional view illustrating the switch actions of the electric toothbrush of the present invention.

In use, referring to FIG. 11, when the switch cover 316 is pressed and moved, the switch rod 33431 will rotate due to the impact so that the curved projection 33421 rotates downwardly in part, causing the switch reeds 3344 to come into contact due to pressure, thus actuating the motor 332, the output gear 3321 of which brings the transmission gear 333 to rotate. And due to the arrangement of the pull arm 3333, which eccentrically displaces to bring the transmission shaft 3334 to reciprocate in a linear direction, thus causing the brush stem 343 of the brush portion 34 to also reciprocate along a linear line. And due to the linear reciprocating movement of the toothed sections 3433 of the brush stem 343, the brush wheels 3442 engaging therewith along with the brush bases 3441 are caused to move in circles. Since the motor 332 rotates at a high speed, the brush bases 3441 rotates in clockwise as well as counter-clockwise directions at high speeds with the brush axles 3422 as axis to perform the cleaning operation.

In view of the above description, the electric toothbrush according to the present invention not only allows the brush wheels 3442 to rotate in opposite directions on fixed points, it also enables the brush portion 34 to be separated from the shell 31 so that the brush portion 34 may be replaceable or a plurality of brush portions 34 may be used in conjunction with a single shell 31. Furthermore, the present invention is equipped with a charging casing 2, which is not taught in any prior art.

After the assembly body 1 of the invention is assembled and electric power is connected, the ozone unit 12 may perform the sterilizing function while the charging unit 13 allows recharging of the charging casing 2. The charging casing 2 may further be used in the electric toothbrush 3. Besides, the brush portion 34, when not in use, may be placed inside the ozone cylinder 121 for sterilization to ensure the hygienic condition of the brush portion 34.

Although the present invention has been illustrated and described with reference to the preferred embodiment thereof, it should be understood that it is in no way limited to the details of such embodiment but is capable of numerous modifications within the scope of the appended claims.

What is claimed is:

1. An electric toothbrush assembly with sterilizing and charging devices, said assembly comprising:

a housing having a hollow ozone chamber in the center, a charging chamber at one side of said ozone chamber, said charging chamber extending downwardly and having two electrical connectors for charging purposes, and two charging grooves at corresponding positions;

an ozone unit comprising an ozone cylinder, an ozone partitioning element, a base plate, an ozone light, and an ozone lid, said ozone cylinder being provided with a slit at the center of an upper portion of an inner wall thereof for engaging and thereby positioning a tab of one of a plurality of partition plates of said ozone partitioning element; said ozone partitioning element comprising said partition plates alternately arranged, a bottom plate of said ozone partitioning element being provided with a bottom hole for passage of ozone thereinto; said base plate comprising a plate having extended walls at opposite sides, a plurality of mounting holes being provided on an outer side of said extended walls for locking said base plate to a bottom of said the housing below said ozone chamber, said base plate further having an ozone hole in the center with a plurality of hollow posts erected around it, a switch slot being provided at a rear end of said base plate for passage of a switch lever which is positioned to match a lower rim of the inner wall of said ozone cylinder, and two switch reeds being disposed at the bottom with an overlapping portion corresponding to said switch lever; said ozone light being connected to a power source by means of circuits and passing through said ozone hole; and said ozone lid having a plurality of mounting pins for insertion into said hollow posts around said ozone hole;

a charging unit, said charging unit being insertably positioned at said electrical connectors of said charging chamber by means of two charging reeds, and extending into said charging chamber via said charging grooves; and a bottom casing comprising a bottom and a cover, said bottom being an open-top casing having a size matching the bottom portion of said housing; and said cover being an open-top box-like structure accommodating a circuit board and being connected to said charging unit and said ozone unit by circuits.

2. An electric toothbrush assembly as claimed in claim 1, wherein a plurality of indication holes are provided below said ozone chamber on a wall of said housing, and an indication light plate is connected to the bottom of a front end of said base plate of said ozone unit, said indication light plate having disposed thereon a plurality of indication lights for matching said indication holes.

3. An electric toothbrush assembly as claimed in claim 1, wherein said charging unit has a compartment for accommodating a battery casing, said battery casing comprising a cylindrical body, a lower electrically conductive plate, two upper electrically conductive plates, a charging terminal, and a cover, said cylindrical body having two pairs of curved wings erected in a vertical direction for holding battery cells tightly, and two parallel tracks at the lower side for positioning said lower electrically conductive plate, said upper electrically conductive plates being locked to the upper side of said cylindrical body; and said cover being locked to the upper side of said cylindrical body; charging being achieved when said upper electrically conductive plates contact said charging reeds.

4. An electric toothbrush assembly as claimed in claim 3, wherein a terminal chamber is formed at the upper end of said cylindrical body for holding a charging terminal, said charging terminal having an end hole into which an external power terminal may insert, and a plurality of extended wings for connecting said upper electrically conductive plates.

5. An electric toothbrush for use with a battery casing as claimed in claim 3, said electric toothbrush comprising:

a shell having an interior accommodating a transmission portion and a battery casing, and being closed by a shell bottom, said battery casing providing power supply to a motor of said transmission portion, said motor bringing a transmission shaft to reciprocate in a linear line via a transmission gear;

a brush portion comprising a brush shell and a brush cover enclosing a brush stem therebetween, and two brush heads, a bottom portion of said brush portion being a hollow tubular structure for fitting onto an upper portion of said shell, said brush portion having two openings in the upper portion thereof; said brush cover being sized to match said brush portion so that they may be coupled, said brush cover having a rod in the middle, and two posts at positions matching said openings of said brush portion; said brush stem having a slot at a bottom end for receiving said transmission shaft, an elongate slot in the middle for matching said post of said brush cover, and an upper section forked to form two parallel arms each of which is provided with a toothed section at an inner side at a different position; said brush heads each comprising a brush base with a brush wheel at one side, the pitch of said brush wheel matching said toothed section of each of said parallel arms, said brush base having a central hole for engaging one of said posts of said brush cover, and a plurality of holes for holding bristles or their equivalents; whereby when said transmission shaft reciprocates in a linear direction, said brush stem reciprocates synchronously therewith so that said brush base of each of said brush heads rotate clockwisely and counter-clockwisely due to the engagement of said toothed sections with said brush wheels.

6. An electric toothbrush as claimed in claim 5, wherein said transmission portion has a transmission shell, and said motor being disposed at a lower portion thereof, said transmission shell having an output gear connected to an output axle of said motor, a transmission gear being pivotally and vertically disposed at the upper portion of said transmission shell for engaging said output gear, said transmission gear having an eccentric hole disposed at one side for receiving one end of a substantially C-shaped pull arm which has the other end inserted into a hole in said transmission shaft so that the output of said motor may be converted into the linear reciprocating movement of said transmission shaft.

7. An electric toothbrush as claimed in claim 5, wherein the upper portion of said transmission shell of said transmission portion is provided with a switch slot, and a transmission cover covering therewith, said transmission cover having a switch mounting hole, with two switch reeds of different polarities disposed at the lower portion at both sides, a switch cock being inserted into said switch mounting hole which has a curved projection of a larger diameter, said switch cock being fitted with a switch knob which has a switch rod projecting vertically therefrom, whereby when said switch rod is turned, said curved projection is caused to press said switch reeds to achieve electrical connection, and vice versa to cut off electrical connection.

8. An electric toothbrush as claimed in claim 5, wherein said switch rod is turned by moving a switch cover on the outer wall of said shell.

9. An electric toothbrush assembly as claimed in claim 1, wherein said housing has a recess disposed at the other side of said ozone chamber, said recess having an electrical connector at a bottom side thereof for connecting to an external power source.

* * * * *